United States Patent [19]
Cloyd et al.

[11] Patent Number: 5,587,285
[45] Date of Patent: Dec. 24, 1996

[54] GENERATION SEROLOGICAL ASSAY FOR MONITORING HIV EXPOSURE

[75] Inventors: Miles W. Cloyd, Galveston, Tex.; Keith M. Ramsey, Mobile, Ala.

[73] Assignee: University of Texas System, Austin, Tex.

[21] Appl. No.: 143,168

[22] Filed: Oct. 26, 1993

Related U.S. Application Data

[62] Division of Ser. No. 829,352, Jan. 31, 1992, abandoned.

[51] Int. Cl.$^6$ .......................... C12Q 1/70; G01N 33/574; G01N 33/567; G01N 33/564
[52] U.S. Cl. .......................... 435/5; 435/7.23; 435/7.24; 435/974; 436/543
[58] Field of Search .......................... 435/5, 974, 7.23, 435/7.24; 436/514

[56] References Cited

U.S. PATENT DOCUMENTS

| | | | |
|---|---|---|---|
| 4,357,310 | 11/1982 | Chan et al. | 436/504 |
| 4,722,888 | 2/1988 | Broder | 435/5 |
| 4,725,669 | 2/1988 | Essex | 435/5 |

OTHER PUBLICATIONS

Groupmon et al, Blood, 66(3):742–44. 1985.
Salahudin et al, Lancet 12 22–291 84. pp. 1418–1420. 1984.
Lee et al, PNAS 81:3856–60 1984.
Homma et al, Seienu 225:716–718 1984.
Tijssew, "Practice & Theory Enzyme Immunoassay", Elsevier 1985, NY pp. 329–332.
Harlow, "Antibodies, A Laboratory Manual", Cold Spring Harbor Press, NY. 1988. p. 184.
Kitchen et al, Nature 312:367–369, 1984.
Essex et al, Science 221: 1061–1064, 1883, (Essex "a").
Essex et al, Science 220:854–862, 1983 (Essex "b").
Gallo et al. (1984), Science, 244:500–3.
Saah et al. (1986), J. Clin. Microbiol., 25(a):1605.
Chou et al. (1988), J. Infect. Disease, 157(4):805–11.
Barin et al. (1985), Science, 228;1094–6.
Kitchen et al. (1986), J. Infect. Dis., 153:788–90.
Ranki et al. (1987), Lancet, 2:589–93.
Imagawa et al. (1989), New J. Med., 320(22):1458–89.
Weiss, R. (Jun. 3, 1989), Science News, 135:340.
Dupont Biotecl Update (May 1989), "Improved HIV p24 Core Profile ELISA: NEK–060, NEK–060A".
Allain et al. (1986), Lancet, 1233:35.
Goudsmit et al. (1987), J. Inf. Disease, 155(3):558–60.
Franchini et al. (1987), Blood, 69(2):437–41.
Sarngadharen et al. (1984), Science, 224:506–8.
Hofbauer et al. (1988), J. Clin. Micro., 26(1):116–20.
Ujhelyi et al. (1987), AIDS, 1:161–5.
Shepp et al. (1987), AIDS, 2:113–7.
Lange et al. (1987), AIDS, 1:15–20.
Ferroni et al. (1988), Vox Sang, 55:143–7.
Harada et al. (1987), Virology, 158:447–51.
Huisma et al. (1987), Vox Sang, 53:31–6.
DiMarzo et al. (1985), Proc. Natl. Acad. Sci., 82:5199–02.
Lasky et al. (1986), Science, 233:209–33.
Cloyd et al. (1977), J. Clin. Microb., 5(1):86–90.
Cloyd et al. (1987), Virology, 161:286–92.
Barre–Sinoussi et al. (1983), Science, 220:868–71.
Popovich et al. (1984), Science, 224:497–500.
Coffin et al. (1986), Nature, 321:10.
Auerbach et al. (1982), N.J.M., 306:248–52.
Burke et al. (1986), JAMA, 256:347.
Salahuddin et al. (1984), Lancet, 2:1418–20.
Mayer et al. (1986), Ann, Intern. Med., 104:194–6.
Groopman et al. (1985), Blood, 66:742–4.
Wolinsky et al. (1988), Fourth International Conference on Aids, Stockholm Abstract No. 1099:137.
Loche et al. (1988), Lancet, 2:418–21.
Miles et al. (1986), Nature, 219:186.
Butler et al. (1978), Immunochemistry, 15:131–6.
Haseltine, W. W. (1989), N. Eng. J. Med., 320:1487–9.
Jemmerson et al. (1986), Science, 232:1001–4.
Poiesz et al. (1980), Proc. Natl. Acad. Sci., USA, 77:7415.
Robert–Guroff et al. (1985), Nature, 316:72–4.
Cloyd et al. (1979), J. Exp. Med., 149:702–12.
Laemmli (1970), Nature, 227:680–5.
Robey et al. (1986), Proc. Natl. Acad. Sci., USA, 84:7023–7.
R. Haschemeyer and A. HAschemeyer, eds (1973) In: Proteins, A Guide to Study By Physical and Chemical Methods, Chapter XV:352–385.
Tanford, C. and Reynolds, J. A., "Characterization of Membrane Proteins in Detergent Solutions, " Biochimica et Biophysica Acta, 457:133–170 (1976).
Helenius, A., et al., "Properties of Detergenets," Methods in Enzymology, LVI: 734–749 (1979).
Hjelmeland, L. M., and Chrambach, A., "electrophoresis and electrofocusing in detergent containing media: A discussion of basic concepts," Electrophoresis, 2:1–11 (1981).

(List continued on next page.)

Primary Examiner—Michael P. Woodward
Attorney, Agent, or Firm—Denise L. Mayfield

[57] ABSTRACT

Disclosed is a highly sensitive anti-HIV antibody detection assay. The assay detects the presence of anti-HIV antibodies through the use of a non-denatured HIV antigenic determinant which immunoreactivity binds anti-HIV antibodies in a biological sample. The non-denatured HIV antigenic determinant has provided a means for detecting anti-HIV antibodies in serum samples testing seronegative for the presence of HIV antibodies directed against denatured HIV antigens p17, p19, p24, p27, p39, gp41, p55, gp120 and gp160. The antigenic determinant may take the form of a cross-immunoreactive live HIV-infected cell line or a biologically engineered peptide possessing conserved or shared HIV surface antigenic determinants. Methods of preparing HIV target antigens are also disclosed, as well as methods for determining the presence of anti-HIV antibodies through the use of these non-denatured HIV target antigens. A test kit for detecting anti-HIV antibodies is also disclosed.

13 Claims, No Drawings

OTHER PUBLICATIONS

Chassagne et al., "A Monoclonal Antibody Against Lav GAG Precursor: use For Viral Protein Analysis and Antigenic Expression In Infected Cells," *The Journal of Immunology*, 136(4):1442–1445, 1989.

Chiodi et al., "Site–Directed ELISA With Synthetic Peptides Representing the HIV Transmembrane glycoprotein," *Journal of Medical Virology*, 23:1–9, 1987.

Clerici et al., "Eavesdropping on Rare 'Silent' HIV–1 Infection," *The Journal of NIH Research*, 3:71–76, 1991.

Cohen et al., "Identification of a Protein Encoded by the vpu Gene of HIV–1," *Nature*, 334:532–534. 1988.

Düzgün et al., "Der Nachweis von HIV–1–Antigen—Bestimmung mit Hilfe von drei verschiedenen Testsystemen," *Klin Wochenschr*, 66:212–215, 1988.

Evans et al., "Clinical evaluationof Abbott and Wellcome enzyme linked immunosorbent assays for detection of serum antibodies to human immunodeficiency virus (HIV)," *J. Clin. Pathol.*, 40:552–555, 1987.

Genesca et al., "Comparison of Four Different Antigen–Capture Assays for the Detection of Human Immunodeficiency Virus Antigen (HIV–Ag)," *Journal of Acquired Immune Deficiency Syndromes*, 2:170–177, 1989.

Hood et al., "," *Immunology*, ?

Houn et al., "Status of Current Clinical Tests for Human Immunodeficiency Virus (HIV: Applications and Limitations," *Annals. of Clinical and Laboratory Science*, 17(5):279–285, 1987.

Mervis et al., "the gag Gene Products of Human Immunodeficiency Virus Type 1: Alignment within the gag Open Reading Frame, Identification of Posttranslational Modifications, and Evidence for Alternative gag Precursors," *Journal of Virologly*, 62 (11):3993–4002, 1988.

Nishanian et al., "Significance of Quantitative Enzyme–Linked Immunosorbent Assay (ELISA) Results in Evaluation of Three ELISAs and Western Blot Tests for Detection of Antibodies to Human Immunodeficiency Virus in a High–Rist Population," *Journal of Clinical Microbiology*, 25(2):395–400, 1987.

Pal et al., "Processing of the structural proteins of human immunodeficiency virus type 1 in the presence of monensin and cerulenin," *Proc. Natl. Acad. Sci. USA*, 85:9283–9286, 1988.

Race et al., "Human Immunodeficiency Virus Infection Elicits Early Antibody Not Detected by Standard Tests: Implications for Diagnostics and Viral Immunololgy," *Virology*, 184:001–007, 1991.

Rey et al., "Characterization of Human Immunodeficiency Virus Type 2 EnvelopeGlycoproteins: Dimerization of the Glycoprotein precursor during Processing," *Journal of Virology*, 63(2):647–658, 1989.

Sligh et al., "Flow Cytometric Indirect Immunofluorescence Assay with High Sensitivity and Specificity for Detection of Antibodies to Human Immunodeficiency Virus (HIV)," *A.J.C.P.*, 91(2):210–214, 1989.

Steckelberg et al., "Serologic Testing for Human Immunodeficiency Virus Antibodies," *Mayo Clin. Proc.*, 63:373–380, 1988.

GENERATION SEROLOGICAL ASSAY FOR MONITORING HIV EXPOSURE

The Government may have certain rights in the present invention as funds for relevant research were provided by NIH Grant No. 5-R01-A1 25289.

This is a divisional of application Ser. No. 07/829,352 filed Jan. 31, 1992, now abandoned.

BACKGROUND OF THE INVENTION

1. Field of the Invention

The present invention relates generally to the field of detection of viral infection. Specifically, the invention relates to the early detection of human immunodeficiency virus (HIV) infection. Even more particularly, the invention relates to the early detection of HIV infection through the detection of antibodies directed against a preparation of non-denatured HIV envelope antigens. The invention also relates to the characterization of an HIV antigen preparation immunoreactive with these early anti-HIV antibodies, and methods of using them in anti-HIV antibody detection.

2. Description of the Relevant Art

A retrovirus is currently believed to be etiologically associated with acquired immunodeficiency syndrome (AIDS). (3, 5). The retroviruses involved are members of the Lentivirus family, variously termed LAV, HTLV-III, and ARV, and collectively termed human immunodeficiency virus (HIV) (3). These virus are commonly transmitted via blood or blood products (1–4), as well as through sexual contact or use of hypodermic needles shared with persons infected with the virus (4). Spread of the HIV virus has now reached epidemic proportions, thus prompting scientists and clinicians around the world to concentrate on developing methods to prevent its continued spread.

A variety of detection or "screening" methods have been developed to control the spread of the virus. For example, some clinicians sought to determine the presence of live virus in patient samples suspected of having been infected (5) However, it was soon found that the virus was not easily isolatable from patient samples, with as high as 40% of infected persons going undetected (5). The low level of detectability by this method is attributable to the typically low circulating concentrations of the virus or virus-infected cells, especially in early infected persons and those in whom anti-viral antibodies were present. In such patients, low levels of circulating virus would be expected owing to the neutralizing activity of the antibody (46). High percentages of false negative HIV exposure diagnoses inevitably resulted. Additionally, the isolation of live virus was very time consuming and expensive, and not readily adaptable to routine laboratory procedure, being limited by the hazardous nature of live virulent cultures.

An alternative procedure which developed to monitor HIV infections was through the detection of various molecular weight denatured HIV virus antigens. The first available assays for blood antigen screening were based on the antigen-capture system. The sensitive detection and quantitation of antigen was pioneered by Berson et al. (45) with the development of the radioimmunoassay (RIA). The RIA is an inhibition assay in which unlabeled antigen (test antigen) competes with a labeled antigen for limited antibody. Some of the more important modifications made to the original RIA were the use of labeled antibodies rather than labeled antigen (39) and the use of solid phase absorbants. The RIA is a useful assay but depends on a principle (competition of two antigens for antibody) that cannot be reversed for the accurate measurement of antibodies.

The presence of HIV DNA (i.e., HIV DNAn) was also tested by enzymatic amplification of HIV-1 DNA using the polymerase chain reaction method. Loche et al. were able to detect HIV DNA through the use of a direct diagnostic test based on hybridization to amplified viral DNA in serum samples 6–14 months before seroconversion as documented by conventional methods (16). Over 23% of a group of persons testing negative (31 of 133) for anti-HIV antibodies by conventional enzyme-linked immunosorbent assay (ELISA) and Western Blot were identified as positive for the presence of HIV antigen as well as HIV DNA by the above methods (17).

Recently, some laboratories have been able to develop antigen detection assays with enhanced sensitivity (19). These assays detected HIV antigen up to three weeks prior to that of conventionally practised antigen detection ELISA's of the day, and with a reduced assay time (i.e., four hours vs. "overnight" incubation) (19). However, such systems measured only denatured HIV antigen of various molecular weights, and were still plagued with high percentages of false-negative diagnoses. The disadvantage of detecting denatured viral antigen is that by the time these antigens are detectable in a patient, the infection has already progressed to its more advanced stages. Cumulative studies by those of skill in the art indicate that a more antibody-sensitive "antigen" or an alternative test method is needed to be developed and used if consistent and accurate early HIV exposure is to be achieved.

While detection of antigen appeared to result in a more reliable diagnosis than live-virus isolation, the need still existed for a more sensitive assay capable of detecting anti-HIV antibodies during early stages of HIV exposure. Quantitation of antibodies is a major objective and problem in immunology since absolute units of antibodies are often difficult to estimate because of the influence of antibody affinity on measurements (39). The ELISA was proposed as the antibody detection test of choice as it provided for the convenient testing of large numbers of serum samples at a time. However, the high frequency of false positive results using denatured HIV-antigen as "target" antigen required further refinement of the assay, as well as a more sensitive "target" antigen to enhance sensitivity of antibody detection (5).

Some investigators have proposed the use of alternative HIV-antigen preparations in standard anti-HIV antibody screening tests (8). The presence of antibodies to gp160 and gp120 (RIP) have been described as the most consistent indicators of HIV-1 exposure in hemophiliacs and in homosexuals (10–11). Chou et al. sought to detect anti-HIV antibody using an infected cell lysate (RIP) or viral lysate (WB) preparation of gp120 HIV with a non-reducing buffer as the "target" antigen. Sensitivity of antibody to gp120 HIV "target" antigen prepared with nonreducing buffer was enhanced by an additional 25% (9). However many persons continued to be reported as "seronegative" for anti-HIV antibodies despite detectable levels of circulating virus. A significant proportion of infected persons with detectable circulating live virus continued to be described as immunologically "seronegative".

Monitoring HIV exposure through antibody detection is plagued by the observation that only very low titers of circulating anti-HIV antibodies are observed in patients in whom detectable circulating levels of live virus are found (12–13). While these and other tests, such as radioimmunoprecipitation and SDS-PAGE (RIP), have led to a decrease in the percentage of reported false negative and false positive diagnoses, there still existed difficulties in determining seropositivity of vague antibody profile patterns (7–8).

A variety of theories were set forth to explain the phenomena of HIV infection without the presence of detectable anti-HIV antibody. One explanation was that in sexually transmitted HIV infection, a long period of latency occurred during which the virus was present, but remained dormant and did not invoke an initial production of detectable anti-HIV antibodies (i.e., pre-seroconversion) (15). Imagawa et al. describe this "silent" infection (i.e. no detectable anti-HIV antibodies by conventional methods) as extending up to 36 months after the positive culture of live HIV virus (17). During this "latency period", persons were described as seronegative for HIV antibody (17).

Haseltine postulates that the failure to detect anti-HIV antibodies in persons with HIV virus indicates the establishment of HIV-1 infection without triggering the immune system, and that loss of antibodies may occur after transient production of the virus and antiviral antibodies, a so-called "silent infection" period (40). This "silent infection" period has been reported to linger years before antibodies are detectable by current methods (18). The state of supposed "silent infection" in which virus is detectable without antiviral antibodies is foreshadowed by earlier reports on high risk, homosexual men, in whom low-titer antibodies were detected, also having virus and/or viral nucleic acids (16).

An alternative method for detecting antibodies is live-cell immunofluorescence. The use of live-cell immunofluorescence has been applied in the analysis of surface antigens of Friend murine leukemia virus-infected (F-MuLV) cells and gibbon ape lymphoma virus infected cells (35). This technique offers the advantage of direct visualization of bound antibody on the surfaces of viable cells. Such assays were adapted for containment of these potentially hazardous virus infected cells (Id.) Applicants later developed a live-cell membrane immunofluorescence assay for the analysis of HIV infected cell surface antigenic determinants (36).

Despite intensive studies into the pathology of HIV, the detection of anti-HIV antibodies in samples obtained months or years prior to classically detectable "seroconversion" in patients from whom live virus is isolated still eludes investigators. It has been assumed that failure of conventional methods (WB, ELISA) to detect viral antigen or anti-HIV antibodies indicates that no antibodies are being produced against the virus. However, false-negative tests for anti-HIV antibody continues to result in failure to detect patients with early transmittable HIV infections. Thus, non-detected HIV-contaminated blood units obtained from persons during the early stages of HIV infection continue to threaten blood recipients of all ages, sexes and sexual preferences.

The development of a new generation serological test able to detect anti-HIV antibodies during the early phases of HIV infection would provide clinical monitoring laboratories and hospitals throughout the world an effective method for halting the spread of AIDS and AIDS-related conditions heretofore frustrated by the complex immunology and biochemical nature of the human immunodeficiency virus.

SUMMARY OF THE INVENTION

The present invention addresses the need for an effective new generation serological assay for early detection of anti-HIV antibodies. Additionally, the present invention has the surprisingly enhanced ability to accurately detect HIV-exposure through the early detection of anti-HIV antibodies. For example, the present invention is able to detect viral infection with 99% accuracy, compared to the 30–40% accuracy detection rates of patient live-virus isolation techniques and 75% detection rates of conventional HIV antigen and anti-HIV antibody detection assays.

Applicants have found that persons previously believed to be seronegative are truly seropositive for anti-HIV antibody. The reagents and methods developed by Applicants to detect early anti-HIV antibodies make possible their early detection possibly years before standard assays discern their presence. Applicants have clearly demonstrated that this early detection of anti-HIV envelope antibodies is possible through the use of live HIV-infected cell "isolates" or undenatured HIV envelope antigenic determinants as a "target" antigen. Prior studies conducted by Applicants have demonstrated that live uninfected cells do not display any immunoreactive activity with known HIV-infected patient serum samples, thus establishing the specificity and virtual elimination of false-positive results of the disclosed method (36).

Applicants have observed that few non-autologous serum samples contain observable antibodies immunoreactive with non-autologous live HIV-infected cells (Id. at 287). Other serum samples obtained from patients in whom live-virus was isolated failed to display immunoreactivity to many of the non-autologous HIV-infected cells at all.

Present studies by Applicants, shown at Tables 3 and 4, demonstrate that not all random HIV-infected cell isolates are recognized by anti-HIV antibodies in sera from all patients. For example, out of 13 HIV-infected cell isolates (Table 1), only about half were found to immunoreactively detect the presence of anti-HIV antibodies in virtually all of the serum samples obtained from HIV-exposed patients (compare Table 2 to Tables 3 and 4, reactivity is expressed as the reciprocal of serum dilution which fluoresced 50% of the target cells in an indirect live-cell membrane fluorescence assay).

This variable degree of reactivity of anti-HIV antibodies in patient sera for different HIV-infected cells and the complete lack of reactivity of some sera for certain HIV-infected cell cultures is hypothesized by Applicants to indicate individuals infected with HIV mount type-specific antibody responses to heterogeneous virus-related antigens expressed on the surface of infected cells. The data also demonstrated that certain HIV infected cells lacked serological epitope(s) that the other viral infected cell isolates expressed.

Applicants' prior studies established that antigenic heterogeneity existed among various HIV-infected cell surfaces, and suggests that these heterogenous, type specific antigens are likely to be the viral env-encoded proteins (Id. at 88). The present invention has focused instead on characterizing the live HIV-infected cell serological epitope(s) shared in common, or "conserved", among a representative number of different HIV-infected cells. The presence of HIV-infected cell antigenic homogeneity has been demonstrated through the use of a cross-immunoreactive HIV-infected cell isolate in testing for anti-HIV antibodies in a number of serum samples obtained from random groups of HIV-infected persons. Blood serum samples testing positive for the presence of antibodies directed against live HIV-infected cell antigen of the present invention had tested negative for the presence of antibodies directed against the denatured HIV antigens p17, p19, p24, p27, p38, gp41 and p55 by Western Blot (WB) analysis. These same blood serum samples also tested negative for the presence of denatured HIV antigen p24. These respective letter and numerical designations represent the following: p=protein; gp=glycoprotein; numerical designation×1,000=molecular weight in daltons. Applicants' experimental data establishing this HIV antigenic "homogenity" has been used to characterize the claimed reagent (target antigen) for monitoring HIV exposure through the detection of anti-HIV antibodies to this reagent in a patient sample. This reagent is also used in the diagnosis of HIV and HIV-1 carriers.

An important feature of the present invention's early detection system lies in the employ of undenatured (i.e. non-denatured HIV-envelope antigen. For purposes of this application, a denatured HIV antigen is defined as an antigen which has an altered quaternary, tertiary or secondary structure from the native form of an envelope antigen of an HIV-infected cell. The particular infected cell is one which has been infected with an HIV selected from the group consisting of $HIV_{MCK}$, $HIV_{PM16}$, $HIV_{PM205}$, $HIV_{213}$, $HIV_{ED-1}$, $HIV_{TP-1}$, $HIV_{AK-1}$, $HIV_{SK-1}$, $HIV_{AC-1}$, $HIV_{214}$, $HIV_O$, $HIV_{G1}$, and $HIV_{III}$. The native form of an envelope antigen of an HIV-infected viral cell are envelope antigens which have not been treated with a reducing buffer, ionic buffer or high levels of non-ionic detergents (i.e., greater than 1% NP-40 or TRITON X-100) or any buffer or agent which would destroy the configurational integrity (i.e., quaternary, tertiary or secondary structure) of the native antigen peptide. The denatured HIV antigen is further described as a protein (p) or glycoprotein (gp) having a particular molecular weight in daltons of its given numerical designation multiplied by 1,000. Many of these denatured HIV antigens are used in monitoring HIV infection. Some of these include p17, p19, p24, p38, gp41 and p55. Applicants have described the invention as detecting anti-HIV antibodies in serum samples seronegative for antibodies to these denatured HIV antigens.

Denatured HIV antigens are further described as native HIV antigens which have been extracted with such reducing agents as dithiothreitol or ionic detergent, or buffers containing high concentrations of non-ionic detergent (i.e. greater than 1% NP-40 or TRITON X-100) or any other buffer or agent which would destroy the conformational integrity (i.e., quaternary, tertiary or secondary structure) of the native antigen peptide.

The "native" form of the HIV-infected cell envelope antigen is maintained through use of a phosphate buffer containing low levels of non-ionic detergent (i.e., about 0.5% NP-40 or TRITON X-100). Ionic detergents are later employed in Applicants' procedures to selectively degrade immunoreactive epitope(s). The loss of immunoreactivity after each treatment will be measured in parallel with "native" envelope protein. However, even mild denaturing treatments may destroy the antigenic epitopes recognized by "early" HIV immune sera, especially where conformational patterns involving non-contiguous sequences within the protein are important.

An undenatured (or non-denatured) HIV envelope antigen for purposes of this application is defined as an HIV envelope antigen with a quaternary, tertiary and secondary structure characteristic of native HIV envelope antigen. A native HIV envelope antigen is one which immunoreactively binds to anti-HIV antibody present in a serum sample seronegative for the presence of antibodies directed against the above-described denatured HIV-antigens (i.e., p17, p19, p24, p38, gp41 and p55).

For purposes of the present application, the secondary structure of the HIV-infected cell antigen is defined as the steric relationship of amino acid residues that are close to one another in the linear sequence of the amino acid. The alpha helix, the beta pleated sheet, and the collagen helix are examples of secondary structure. Tertiary structure refers to the steric relationship of amino acid residues that are far apart in the linear sequence. Quaternary structure refers to the manner in which the polypeptide chains of the protein (or peptide) are packed together.

The antigenic reagent of the present invention comprises a non-denatured HIV-envelope antigen preparation, which may be prepared by a number of non-denaturing methods. The most preferred HIV antigen preparation comprises a pure culture of live HIV-infected cells found to be cross-immunoreactive with antibodies in a representative number of serum samples from HIV-infected persons. This HIV infected live cell culture comprises the target antigen of the described live cell immunofluorescence assay. In particular, these HIV-infected cell isolates are cells which have been infected with an HIV given the designations $HIV_{TP-1}$, $HIV_{PM16}$, $HIV_{PM205}$, $HIV_{213}$, $HIV_{ED-1}$, $HIV_{TP-1}$, $HIV_{CP1}$, $HIV_{MCK}$, $HIV_{AK-1}$, $HIV_{SK-1}$, $HIV_{AC-1}$, $HIV_{214}$, $HIV_O$ and $HIV_{G1}$. The HIV infected cell isolates found to be most cross-immunoreactive were those cells infected with $HIV_{TP-1}$, $HIV_{213}$ and $HIV_{AC-1}$. These three particular viral species are being deposited with the ATCC in compliance with the Budapest Treaty. The address of the depository is:

American Tissue Culture Collection
12301 Parklawn Drive
Rockville, Md. 20852

The depository data is shown in the following list:

|  | deposition number | date of deposition |
| --- | --- | --- |
| $HIV_{TP-1}$ | VR2245 | August 3, 1989 |
| $HIV_{213}$ | VR2247 |  |
| $HIV_{AC-1}$ | VR2246 | August 3, 1989 |

These deposits were made to satisfy compliance with Applicants' "best mode" requirements under 35 U.S.C. §112. The viral species are also readily available in Applicants' laboratory at The University of Texas Medical Branch at Galveston, Department of Microbiology.

Applicants have also detected the presence of shared surface antigenic determinants among a representative number of HIV-infected cell samples. These shared antigenic determinants are characterized as part of the viral envelope, despite the observed variability of the viral envelope region (compared to core) and difficulties associated with the characterization of the limited number of "shared" envelope antigenic epitopes. Recognition of these shared HIV antigens has led to the proposed development of a procedure by which the hypothesized particular conserved HIV-antigenic determinants may be characterized and a biologically engineered HIV antigenic determinant constructed. Such a determinant would constitute an avirulent reagent for use in standard clinical assays, for example, the ELISA antibody detection assay. The present invention further features a modified ELISA anti-HIV antibody detection kit employing the characterized "shared" HIV antigenic determinant as the "target" antigen.

The most preferred source of non-denatured, HIV-antigen reagent comprises a live HIV-infected cell culture isolate or an avirulent preparation of a non-denatured HIV antigen possessing like antigenic epitopes to the live-cell isolate. The term "avirulent" as used in this application is defined as a substance which does not produce or cause HIV infection in those organisms which come in contact with it. Such are used as antigenic reagents in the presently claimed anti-HIV antibody detection kit.

The HIV "target" antigen may comprise a biologically-engineered avirulent antigenic determinant. This determinant is to be biologically constructed from experimental data generated from absorption analysis of HIV reactive immune-complexes of conserved or "shared" non-denatured HIV antigenic determinants (i.e., envelope-encoded antigenic determinants).

A preferred embodiment of the HIV-antigenic reagent ("target" antigen) is to be obtained through mapping of the shared epitopes of envelope glycoproteins by protease fragmentation analysis of antibody-HIV antigen complexes and/or recombinant DNA technology. The HIV-infected culture of cells are obtainable through the infection of a culture of cells with an HIV. The HIV infected cell isolate comprises a live HIV culture reactive (i.e. exhibiting an immunological response) with the anti-HIV antibody present in a representative number of known HIV infected samples (i.e., anti-HIV antibodies reactive with standard HIV-antigens). For purposes of the application, a representative number of biological samples comprises at least four samples taken from non-autologous patients.

The most preferred method of preparing the live HIV infected cell culture comprises obtaining a biological sample from a patient, determining the presence of viable HIV, and isolating the virus apart from other sample components. A cell line is then infected with the particular isolated virus to establish an HIV-infected cell line. A biological sample for detecting virus as used in this application comprises either a peripheral blood sample or a bone marrow sample, or any body fluid in which virus may be identified in. The most preferred source of a biological sample for infected-cell isolate preparation is a peripheral blood sample.

The preferred method of preparing the live HIV cell "isolate" (i.e. a culture that is cross reactive with a representative number of known HIV-infected persons) comprises immunologically testing the proposed sample of live HIV cell isolate with a representative number of serum samples obtained from persons with known HIV infection.

A representative number of peripheral blood samples have been characterized to determine the presence of shared HIV envelope antigenic determinants. The HIV target antigen used to detect anti-HIV antibodies was found to be immunoreactively recognized by each of a representative number of biological samples. Those viral "isolate" samples which display binding reactivity (immunological) with anti-HIV antibody in a representative number of known seropositive samples identified the particular HIV antigenic determinants required to elicit the immunological "recognition" or reactivity of early anti-HIV antibodies. These live cross-reactive HIV isolates were then adapted to continuous cell line cultures. These live HIV-infected isolates constitute one preferred embodiment of the antigen to be used as a reagent ("target" antigen) in the claimed early anti-HIV antibody detection assay.

An additional method for identifying a representative HIV live-cell "isolate" with "shared" HIV antigenic determinants involves obtaining a serum sample from an infected individual (i.e., circulating virus) and immunoreactively testing an autologous serum sample for anti-envelope antibodies, using the preparation of live HIV isolated as the "target" antigen. This testing is preferably by the method of live-cell immunofluorescence described by Cloyd et al. (36). Samples testing positive by autologous live-cell immunofluorescence are then cross-tested with other non-autologous HIV culture samples to discern the presence of antibodies.

The HIV antigenic isolates are to be maintained in a pure culture until use. For purposes of this application, a pure culture is defined as a population of HIV-infected cells free from non-living impurities interfering with the subject immunoreactivity and deleterious viable contaminating microorganisms.

The detection of anti-HIV antibodies by these methods indicate the presence of conserved envelope antigens among a number of HIV infected cells. The antigen reagent ("target" antigen) of the claimed early HIV antibody detection assay comprises the identification of these conserved envelope antigens. For purposes of this application, "target" antigen is defined as the particular antigen to which anti-HIV antibodies are directed against, and with which said antibodies immunoreactivity bind.

The present invention also comprises the discovery of "shared" conserved HIV-envelope antigenic determinants and the molecular characterization thereof. A further important feature of the present invention is an avirulent HIV antigen preparation with sufficient antigenic determinants to immunoreactively bind anti-HIV antibodies present among a representative number of early HIV-infected persons.

For purposes of this invention the term "isolate" is defined as either a live-cell viral isolate obtained through the selective culture of live HIV infected cells found immunologically cross-reactive with antibodies in a representative number of biological samples, (i.e., serum samples) or as a biologically engineered isolate of conserved HIV antigenic determinants serving this same end. For purposes of this invention, a biologically engineered isolate includes a genetically engineered isolate or mutant, or variant thereof with like antigenic characteristics, containing a DNA segment which encodes for an antigenic determinant of any conserved region of the non-denatured HIV viral envelope protein. A "conserved" HIV envelope antigenic region is a segment of the viral envelope observed to immunoreactively bind to anti-HIV antibodies present in a representative number of serum samples taken from patients with detectable live HIV virus. The described HIV antigen preparations may then be used in an ELISA assay or live-cell immunofluorescence assay to detect the presence of anti-HIV antibodies in a biological sample. This assay is described in detail infra at Example 10.

The present invention also comprises a method of detecting anti-HIV antibody in a biological patient sample, comprising immunoreactivity testing the biological sample with a culture of live-HIV virus. This method, by way of example, comprises an indirect viable-cell membrane immunofluorescence assay. By way of example, the biological sample in which antibodies are to be detected may comprise a blood serum sample or any body fluid. Most preferably, the biological sample comprises a human blood serum sample. Detection of anti-HIV antibody may alternatively comprise immunoreactively testing a serum sample with a non-denatured HIV antigenic determinant (i.e. "target" antigen). Additionally, the "target" antigen may instead comprise an autologous or non-autologous culture of live HIV infected cells.

A method of preparing the HIV target antigen reagent of the present invention is also included herewith. The present invention additionally comprises a kit for early anti-HIV antibody detection. The subject kit includes the HIV antigenic determinants as described above and includes a secondary labeled antiserum. The label may comprise either an isotope, enzyme or a fluorescent moiety. The enzyme by way of example may be a peroxidase. The kit further comprises a multi-well microtiter plate and a group of vials containing biological reagents used in the assay. Each well of the microtiter plate is coated with a quantity of non-denatured HIV envelope antigen, and comprises the "target" antigen of the assay.

Abbreviated terms used throughout the specification are defined as follows:

FITC=fluorescein isothiocyanate
ul=microliter
HIV=human immunodeficiency virus
dH2O=deionized water
env=envelope
ELISA=Enzyme linked immunoadsorbent assay
WB=Western blot
p=protein
gp=glycoprotein
PHA=phytohemagglutamin
PBM=peripheral blood mononuclear cells

DESCRIPTION OF THE PREFERRED EMBODIMENTS

The present invention is directed toward a non-denatured preparation of HIV-envelope antigenic determinants and the use thereof in an improved assay for the early detection of anti-HIV antibodies. More particularly, the assay is directed to an improved serological assay for the detection of anti-HIV antibodies in patients with sera testing negative for HIV p24 antigen (antigen-capture ELISA) and for antibodies directed against p17, p19, p24, p38, gp41 and p55 (Western Immunoblotting) by currently practiced methods.

The proposed diagnostic test surprisingly is able to detect the presence of anti-HIV antibodies in patients who do not display any clinical symptoms of the infection and who are further described as "seronegative" despite the presence of live virus. Thus, the present invention also constitutes a significant step forward in enhancing assay sensitivity in detecting anti-HIV antibodies.

Genetic analysis of the antibody genes discerned through the use of serological reagents has revealed distinctive antigenic markers on immunoglobin molecules. Two of these antigenic markers, termed isotypes and idiotypes, are examined in the development of a biologically engineered HIV "target" antigen. The term "isotype" as used throughout the specification and claims is an antigenic determinant of the antibody that distinguish the constant regions of the different heavy-chain classes and light chain types of a particular antibody. The term "idiotype" refers to the antigenic specificity of an antibody that distinguish one V domain from other V domains. This specificity is controlled by the heavy chain variable segment of the antibody.

The "target" antigen of the present invention may comprise a live HIV-infected culture of cells or a preparation such as one which is biologically engineered or a non-denatured HIV-envelope having identifying antigenic characteristics of the live HIV-infected culture of cells. A biologically engineered "target antigen" includes genetically engineered peptides or proteins possessing sufficient antigenic determinants so as to immunoreactively bind early anti-HIV antibodies. These antigenic determinants are those expressed on live HIV infected cells found to be "shared" or conserved among a representative number of HIV-infected cells.

In one particularly preferred embodiment of the serological assay, the human immunodeficiency virus type 1 is isolated from peripheral blood lymphocytes. The virus may be isolated by a variety of procedures. However, the most preferred method of virus isolation is detailed in Example 1, infra, and is described by Gallo, et al. (*Science*, 254:500–503(1984)). These HIV-infected cells may be isolated from any appropriate biological sample. Preferred sources of HIV-infected cells are peripheral blood samples or bone marrow lymphocyte samples. The most preferred source of HIV-infected cells is peripheral blood. Cells and conditioned media from these cells and conditioned media from lymphocytes are assayed for the presence of HIV. Samples exhibiting more than one of the following were considered positive for the presence of HIV:

1. repeated detection of a $Mg^{2+}$-dependent reverse transcriptase activity in supernatant fluids;
2. virus observed by electron microscopy;
3. intracellular expression of virus-related antigens detected with antibodies from "seropositive" donors or with rabbit antiserum to HIV I; or
4. transmission of particles, detected by RT assays or by electron microscopic observation, observation to fresh human cord blood, bone marrow, or peripheral blood T lymphocytes.

All isolates are distinguishable from HTLV-I or HTLV-II and are classified as HIV on the basis of morphological features observed by electron microscopy, cytopathic effects (41); antigenic cross reactivity (42); and nucleic acid analysis (17).

The following Examples 1–11 demonstrate various aspects of the most preferred embodiments of the present invention. Example I outlines the preferred method of preparing an HIV isolate. Example 2 demonstrates the method by which the cross-immunoreactivity of a particular HIV infected cell culture with anti-HIV antibodies in a variety of serum samples is performed. Example 3 details the method by which antibody reactivity is detected in patient samples using live-HIV infected cells as the target antigen. The HIV isolate which elicits the greatest number of positive immunoreactive binding with anti-HIV antibody is used as the preferred target antigen of the anti-HIV antibody detection assay. Example 4 details the use of the prepared HIV target antigen "isolate" in the early HIV exposure detection assay using live-cell immunofluorescence.

Example 5 demonstrates the method by which the conserved regions of the HIV envelope, encoded by the env gene, are to be characterized through absorption analysis. Example 6 demonstrates the method by which a non-infectious preparation of conserved HIV antigen is to be prepared from identified HIV infected cell isolates. Example 7 outlines the method by which a non-infectious preparation of conserved regions of HIV envelope may be used in an ELISA anti-HIV antibody detection assay.

Example 8 demonstrates comparative statistics on the accuracy of HIV detection results obtained by virus isolation alone (employing the Gallo et al. method (5)) versus those results obtained through the anti-HIV antibody detection system of the claimed invention. The nonvirulent-HIV antigen preparations described in Example 6 are used in the HIV detection kit presented in Example 9. Example 10 details the steps of the RIA to be used in the detection of anti-HIV antibody in a patient sample. Example 11 describes the method by which a culture of cells may be infected with HIV to form an HIV-infected cell culture. This culture may then be used as "target" antigen in the early detection of anti-HIV antibodies by live-cell immunofluorescence.

EXAMPLE 1

HIV Isolation from Peripheral Blood Mononuclear Cells

The present experiment was performed to determine the most effective method for isolating viable HIV in a patient sample. Patients testing positive for the presence of live HIV are used in the development of HIV "target antigen" isolates in experimentally useful concentrations of live HIV from the identified patient sample.

The most preferred source of live HIV is from human peripheral blood samples taken from HIV-infected persons. While HIV may be isolated from a blood sample by any number of procedures, the most preferred method of achieving isolation of virus is outlined as follows.

Isolation of HIV is accomplished by first identifying a person infected with HIV and obtaining a whole hepararinized blood sample from them. The blood sample is then centrifuged through Ficol to separate the peripheral blood mononuclear cells (PBM's). The band of PBM's is then removed and the cells washed one time, counted, and resuspended to $1\times10^6$ cells/ml. in RPMI 1640 media supplemented with 15% fetal bovine serum and 4 micrograms/ml. PHA. The PBM cells are then cultured in a flask for 48 hours at 37° in a $CO_2$-humidified incubator. The cells are then centrifuged and resuspended in media containing 10% IL-2 solution.

Aliquots of fluid plus cells are harvested twice weekly from these cultures and each is tested for the presence of HIV by either reverse transcriptase assay or by HIV antigen-capture assay. These later procedures are well known to those of skill in the art and are reviewed by Poiesz et al. (44), which reference is hereby specifically incorporated herein by reference. The cultures are then maintained 4–6 weeks.

Any harvest which possess evidence of HIV is then transferred to various established cell lines in order to isolate the virus in a cell line which may then be expanded indefinitely.

EXAMPLE 2

Preparation of Cross-Reactive Live HIV Isolate as a Target Antigen for Anti-HIV Antibody Detection The following experiment was conducted to define an HIV-live cell isolate reactive to the antibodies present in a representative group of HIV-infected persons. Identification of such an isolate is instrumental in the development of a target antigen processing antigenic determinants recognized by early anti-HIV antibody. Applicants used a live-cell immunofluorescence assay in conjunction with an EPICS Flow Cytometer to determine the presence of antibodies on the surface of live HIV infected cells in patient isolates. HIV patient isolates were prepared by the method outlined in Example I (supra).

Specifically, HIV was isolated from lymphocytes of high-risk individuals who were seronegative for HIV-I antigen p24 and anti-HIV antibody (p17, p19, p24, p27, p38, gp41, p 55) by commercial clinical tests. The live viral HIV isolates were then used to test autologous serum samples from the donors for the presence of anti-HIV antibodies by a live-cell immunofluorescence assay. These HIV isolates were then used as "target" antigen to test for the presence of anti-HIV antibodies in sera samples taken from a representative number of high-risk but "seronegative" (by conventional anti-HIV antibody assay) human subjects.

The isotype of antibodies detected in these "early infected" individuals will then be determined. This will be accomplished by live cell membrane fluorescence on HIV-infected cells with autologous sera samples and FITC-conjugated secondary antibodies which are isotype specific. In this manner, the precise type of anti-HIV antibodies will be determined and not any others that may be present in the sample.

The extent of reactivity of these antibodies to various antibodies with the various HIV isolates will be performed by live-cell membrane fluorescence using H9, Jurket or CEM cells infected with 30 different isolates of HIV-1. Each sera is to be titrated from 1:20 to 1:2,000 on these infected cells, and a reciprocal of the highest dilution which reacts by flow cytometry will be the serum titer for each of the different HIV isolates.

Cells and Viruses

HTLV IIIb and H9 cells were obtained from the National Institute of Health. HIV pm-16, HIV pm-13 were obtained by infecting H9 cells with supernatants from patient PBL cultures. The remaining isolates were obtained by co-cultivation of PHA-stimulated PBL's obtained from patients with H9 cells. All viruses were passed cell-free at least once at a limiting dilution onto H9 cells and were then maintained as chronically infected lines.

Membrane Immunofluorescence Assay

An indirect microimmunofluorescence assay using live HIV infected cells as target antigen was used. The particular target antigens used in these assays appear in the list of HIV-isolates at Table 1. This list is provided by way of example and not limitation, and provides examples of the target antigen used in the claimed detection methods. The assay entails incubating $1\times10^5$ live cells with 50 ul. of diluted patient sera in wells of a 96-well microtiter plate at least 45 minutes, washing and centrifugation of the plate in a special plate holder, and incubating the plate at least another 45 minutes in 50 microliters of FITC-conjugated goat anti-human polyvalent IgG (diluted 1:100, Sigma). Following a wash, the cells are fixed with 2% formalin and mounted on microscope slides and the number of fluorescing cells quantified under a Zeiss photomicroscope with u.v. epi-illumination.

Results from tests employing live HIV isolate with non-autologous sera samples indicated the presence of anti-HIV antibodies in patients who had tested "seronegative" by standard serological HIV antibody-testing techniques for antibodies against denatured HIV antigen. The results are displayed at Table 2. The isolates identified in this study were found to be immunoreactive (i.e., demonstrate immunospecific binding) with known-HIV infected ("seropositive") patient samples. These results confirmed Applicants' hypothesis that the isolates were useful as true and representative antigenic targets for anti-HIV antibodies. Applicants hypothesize that these antibodies remained non-detectable in routinely practiced anti-HIV antibody detection assays because of the particular denatured HIV antigen used therein as "target" antigen.

Tables 1 and 2 shows a listing of the various HIV isolates developed by the Applicants. These HIV isolates are maintained and are available in the Applicants' laboratory at the University of Texas Medical Branch at Galveston, Tex., Department of Microbiology.

TABLE 1

HIV ISOLATES AVAILABLE IN THE LAB

| Virus Designation | Origin Geographic Region | Tissue[1] | Disease Status[2] (CDC Stage) | Cells Propagated In |
|---|---|---|---|---|
| HTLV-III$_B$ | | | | |
| HIV$_{PM16}$ | MD | PBM | Not Known | H9 |
| HIV$_{PM205}$ | MD | PBM | Not Known | H9 |
| HIV$_{PM213}$ | MD | PBM | Not Known | H9 |
| HIV$_{ED-1}$ | MD | LN | 3 | H9 |
| HIV$_{TP-1}$ | NC | PBM | 4 | H9 |
| HIV$_{CP-1}$ | NC | PBM | 4 | H9 |
| HIV$_{MCK}$ | NC | PBM | 4 | H9 |
| HIV$_{AK-1}$ | NC | PBM | 4 | H9 |
| HIV$_{SK-1}$ | NC | PBM | 2 | H9 |
| HIV$_{AC-1}$ | NC | PBM | 4 | H9 |
| HIV$_{214}$ | NC | PBM | Not Known | H9 |
| HIV$_O$ | NC | PBM | Not Known | H9 |
| HIV$_{G1}$ | NC | PBM | Not Known | H9 |

[1]LN = lymph node
PBM = peripheral blood mononuclear cells
[2]CDC staging:
Group 2 (asymptomatic)
Group 3 (lymphadenopathy)
Group 4 (ARC/AIDS)

TABLE 2

REACTIVITY OF PATIENT SERA FOR ENV ANTIGENS OF VARIOUS HIV-1 ISOLATES

| Serum from sero-negative patients | Uninfected Cells | Cells Infected With | | | | | |
|---|---|---|---|---|---|---|---|
| | | HIV R006 | HIV R023 | HIV R078 | HIV R082 | HIV PM213 | HIV AC-1 |
| R006 | — | 1,600 | 400 | 200 | 40 | 80 | 160 |
| R023 | — | 100 | 6,400 | 50 | 160 | 640 | 160 |
| R078 | — | 40 | 40 | 800 | — | — | 40 |
| R082 | — | 640 | 40 | 80 | 1,280 | 320 | 320 |

*Reciprocal of endpoint serum dilution that reacted with live cells by immunofluorescence

EXAMPLE 3

Antibody Reactivity of Sera from HIV-Infected Individuals for ENV Antigens Expressed on Live HIV-Infected Cells The following experiment was designed to determine the minimum number of antigenic epitopes required to invoke anti-HIV antibody recognition and to determine the distribution of these sites among the different HIV isolates (i.e., HIV$_{CP-1}$, HIV$_{AC-1}$, HIV$_{MCK}$, HIV$_O$, HIV$_{214}$, HIV IV and HIV$_{205}$).

Live cell immunofluorescence was performed for each patient sera sample with each of the various HIV-infected isolates as "target antigen" (described in Example 4, infra). The results obtained from this study appear at Tables 3 and 4. The data indicates that the most cross-immunoreactive HIV-infected cell isolates were cells infected with the HIV$_{MCK}$, HIV$_{PM16}$, HIV$_{PM205}$, HIV$_{213}$, HIV$_{ED-1}$, HIV$_{AK-1}$, HIV$_{SK-1}$, HIV$_{214}$, HIV$_O$, HIV$_{G1}$, HIV$_{III}$, HIV$_{AC-1}$, and HIV$_{TP-1}$ virus. The most immunoreactive HIV-infected cell isolates among this group of HIV virus were the HIV$_{AC-1}$, HIV$_{213}$ and HIV$^{TP-1}$ virus.

Applicants postulate the variable degree of reactivity of these sera for different isolate HIV-infected cells and the complete lack of reactivity of some sera for certain viral isolates suggest that individuals infected with HIV mount type-specific antibody responses to heterogeneous virus-related antigens expressed on the surface of infected cells.

TABLE 3

REACTIVITY OF SERA FROM HIV-INFECTED INDIVIDUALS FOR ENV ANTIGENS EXPRESSED ON HIV-INFECTED CELLS

| Sera (Patient #) | Uninfected H9 Cells | H9 Cells Infected With: | | | | | | |
|---|---|---|---|---|---|---|---|---|
| | | AC-1 | CP-1 | MCK | 0 | 214 | III | 205 |
| C Control | — | — | — | — | 10 | — | — | — |
| 11) | — | 20* | — | — | — | — | 80 | 20 |
| 1) | — | 10,240 | 80 | 40 | — | — | 40 | 80 |
| K) | — | 40 | — | — | 160 | 160 | — | 5,120 |
| 8) | — | 10,240 | 20 | — | 20 | — | 20 | 40 |
| 12) | — | 160 | — | — | 40 | — | — | — |
| 5) | — | 160 | 80 | 80 | 40 | — | 160 | 160 |
| 2) | — | >20,480 | 80 | 320 | 160 | — | 40 | 1,280 |
| 10) | — | 5,120 | — | 80 | 160 | 10 | 40 | 40 |
| 6) | — | 2,560 | — | — | 20 | — | 320 | 80 |
| 13) | — | 20,480 | — | — | — | 10 | 80 | 160 |
| 15) | — | 160 | — | — | — | — | 160 | — |
| 20) | — | 20,480 | 20 | — | — | — | — | — |
| 17) | — | 10,240 | 40 | 20 | 80 | 2,560 | 20 | 320 |
| 18) | — | 2,560 | — | 20 | 160 | 10,240 | — | 160 |
| 21) | — | 1,280 | — | 1,280 | 640 | 1,280 | — | — |
| 9) | — | 1,280 | — | — | — | 10,240 | 40 | 20,480 |

TABLE 3-continued

REACTIVITY OF SERA FROM HIV-INFECTED INDIVIDUALS FOR ENV ANTIGENS EXPRESSED ON HIV-INFECTED CELLS

| Sera | Uninfected | H9 Cells Infected With: | | | | | | |
|---|---|---|---|---|---|---|---|---|
| (Patient #) | H9 Cells | AC-1 | CP-1 | MCK | 0 | 214 | III | 205 |
| 14) | — | 2,560 | 10 | 20 | 20 | 160 | 20 | 1,280 |
| 16) | — | 1,280 | — | 40 | 40 | 5,260 | 160 | 2,560 |

*Reciprocal of highest dilution of serum that fluoresced live cells in immunofluorescence.
Negative means no fluorescence was observed even at the highest serum concentration used (1:20).

TABLE 4

REACTIVITY OF SERA FROM HIV-INFECTED INDIVIDUALS FOR ENV ANTIGENS EXPRESSED ON HIV-INFECTED CELLS

| Sera | Uninfected | H9 Cells Infected With: | | | | | |
|---|---|---|---|---|---|---|---|
| (Patient #) | Jurket Cells | HTLV-III$_b$ | TP-1 | AK-1 | SK-1 | 213 | G1 |
| MC Control | — | — | — | — | — | — | — |
| 11) | — | — | — | — | — | 20 | — |
| 1) | — | 5,120* | 2,560 | 320 | 20 | 5,120 | 1,280 |
| K) | — | 160 | 1,280 | — | 20 | 5,120 | — |
| 8) | — | 20,480 | 2,560 | 160 | — | 10,240 | 40 |
| 12) | — | 20 | 320 | — | — | — | — |
| 5) | — | >20,480 | 640 | 320 | — | >20,480 | 160 |
| 2) | — | 160 | 1,280 | 5,120 | 20 | 640 | 640 |
| 10) | — | 20,480 | 320 | 20,480 | 160 | 20,480 | 80 |
| 6) | — | 1,1280 | 320 | — | — | 2,560 | — |
| 13) | — | >20,480 | 2,560 | 160 | — | >20,480 | 80 |
| 15) | — | 640 | 2,560 | 40 | — | 10,240 | 40 |
| 20) | — | 5,120 | 160 | 2,560 | 160 | >20,480 | 20 |
| 17) | — | 160 | 5,120 | 1,280 | 320 | 2,560 | 640 |
| 18) | — | 160 | 1,280 | 320 | 320 | 2,560 | 160 |
| 21) | — | 2,560 | 2,560 | 80,160 | 320 | 2,560 | 10± |
| 9) | — | 640 | — | 1,280 | 10 | 2,560 | — |
| 14) | — | 640 | 5,120 | 10,240 | 1,280 | 2,560 | 2,560 |
| 16) | — | >20,480 | 1,280 | 1,280 | 80 | <640 | 80 |

*Reciprocal of highest dilution of serum that fluoresced live cells in immunofluorescence.

EXAMPLE 4

Live-Cell Immunofluorescence Assay for HIV Exposure

The present experiment was designed to develop an early detection assay for the presence of antibodies directed against HIV in a patient sample. The method comprises a microtechnique for an indirect viable-cell membrane immunofluorescence titration assay. The assay was adapted for containment of cells infected with HIV virus to control the hazardous nature of the selected antigenic determinant.

HIV isolates were prepared by the method outlined in Example 1. The cross-reactive viral isolates prepared by the method of Example 2 comprised the target antigen of the subject assay. The target antigen (viral isolate) was prepared to a concentration of $2\times10^7$ cells/ml. A volume of live cells were added to each well and pelleted, for example, by centrifugation and the supernatant pipetted off so as to leave an undisturbed pellet of HIV-infected cells. $1\times10^5$ live cells were then incubated with 50 ul. of diluted sera (patient test sample) in wells of a 96-well microtiter plate. The HIV-infected cells and sera (biological sample) were allowed to incubate for at least 45 minutes, and then were washed and pelleted, for example by centrifugation in a special plate holder. The prepared plate was then allowed to incubate for at least an additional 45 minutes in 50 ul. of FITC-conjugated goat anti-human polyvalent IgG (diluted 1:100) (Sigma).

Following at least one wash in a non-denaturing buffer, the cells were fixed with 2% formalin and mounted on microscope slides. The number of fluorescing cells were then quantified under a Zeiss photomicroscope with uv epi-illumination. The presence of conjugated fluorescing cells indicated the presence of antibodies directed against HIV in the biological sample.

EXAMPLE 5

Proposed Characterization of Shared HIV Envelope Antigenic Epitopes

The present experiment is devised to characterize the particular "conserved" envelope antigenic determinants (epitopes) shared between 30 samples taken from persons at high risk for HIV exposure. A group of 30 samples comprises a "representative number" of samples as defined supra in the specification. "Conserved" antigens as the term is used in this application relates to the minimal number of antigenic epitopes required for anti-HIV antibody recognition of the "target" HIV antigen. The distribution of the antigenic epitopes among the different isolates was also examined.

It is hypothesized by Applicants that the antibody-detecting ability of the particular HIV isolate developed in Example I is attributable to the presence of conserved envelope antigenic epitopes present on the non-denatured HIV infected cell surface, and that the presence of these conserved regions makes possible the anti-HIV antibody recognition among patient samples observed in the live-cell immunofluoresence assays described in Example 4. The following protocol is proposed to determine what these particular antigen epitopes are on a molecular basis, and also to determine the following:

1. Role of envelope protein quarternary structure on these epitopes by examining antibody reactivity for gp 120 and/or gp 41 dissociated from each other;
2. Role of gp 120 carbohydrates in formation of these epitopes;
3. Role of disulfide-mediated folding of gp120 in epitope formation;
4. Mapping these epitopes on the envelope glycoprotein by protease fragmentation analysis and/or by recombinant DNA technology.

The characterization of "conserved regions" will begin with the live HIV isolates described and used in the assay of Example 4. Patient samples testing positive for the presence of HIV antigen by that method will next be tested for reactivity against a (representative group) of HIV isolates. The HIV-infected cells demonstrating positive cross-immunoreactivity with the greatest number of serum samples will then be selected for HIV envelope epitope analysis (Table 5, Step 1). The particular scheme to be followed for the characterization of HIV envelope epitopes reactive with a representative number of anti-HIV antibodies is presented at Table 5, which table is referred to throughout the following description.

Absorption Analysis

Absorption studies will be performed to determine the minimum number of different antigenic epitopes the anti-HIV antibodies are recognizing and the distribution of these sites among the different isolates. The procedure for sera absorption has been described elsewhere (Cloyd et al. (1979) *J. Exp. Med.*, 149:702–712). Patient sera (dilution determined from the prefitering results against the various HIV isolates) will be absorbed with varying concentrations of either infected or uninfected cells. The sera will then be retested on the absorbing virus-infected cells as well as on cells infected with other viruses. After all the cross-absorption assays have been performed, sequential absorptions with different isolates will be performed to determine which antigenic epitopes are shared between a representative group of live-HIV infected patient cell samples.

More specifically, the procedure for sera adsorptions involves incubating 2 vol. of diluted sera (biological sample) with dispersed cells equal to 1 vol. of packed cells for 12–16 hours at 4° C. Each serum sample will be absorbed in duplicate. One set will be absorbed once and the other set twice. The absorbed sera will then be tested on target cells. If residual antibody activity declined with the second absorption then further absorptions were performed until residual reactivity if any, ceased to decline.

HIV-infected cells (peripheral blood lymphocytes or T cell lines) serve as a source of viral proteins (i.e. "target" antigen). To maintain antigenic epitopes, native (nondenatured) proteins will be isolated using a phosphate buffer containing low levels of nonionic detergent (0.5% NP-40 or Triton X-100, Table 5, Step 2). Envelope proteins will be concentrated and purified by immunoaffinity chromatography as previously described by Robey et al., (1986) (*Proc. Natl. Acad. Sci. USA*, 84: 7023–7027). This resulting preparation of native HIV-protein (i.e. "target" antigen) will be tested directly for immunoreactivity (i.e. binding affinity) with "early"-infected sera to confirm antibody specificity using either standard immune precipitation (Cloyd et al., (1982) *J. Virol.*, 41: 1112–1117) or Western blotting (W.B.) (Burnette (1981), *Anal. Biochem.*, 112: 195–208) procedures (Table 5, Step 3).

SDS-PAGE

Cells ($1\times10^7$) chronically infected with HIVs were washed and incubated for 15 min. at room temperature in phosphate-buffered saline containing 200 ug./ml. lactoperoxidase (Sigma), 3 mCi $^{125}$I-Na and 0.001% $H_2O_2$. The cells were then washed and lysed in cold 0.5% NP-40. Lysates were precleared by a 15 min. incubation with normal human serum (100:1, v/v, followed by a 30-min. incubation on the ice with a 10% suspension of formalin-fixed, washed *Staphylococcus aureus* Cowan strain (10:1 lysate/staph, v/v), and then ultracentrifugation at 8,000 g for 30 min. (Table 5, Step 4). Samples ($1–2\times10^6$ cell equivalents) of precleared lysate will be immunoprecipitated with 3 ul. of sera or 100 ul. of tissue culture monoclonal antibody supernatant overnight at 4° C. Precipitates will be recovered with *S. aureus* and analyzed by SDS (10%)-PAGE under reducing conditions (5% 2-mercaptoethanol).

Electrophoresis

Both nondenaturing and denaturing polyacrylamide gel electrophoresis (48) (Laemmli, 1970) will be used to separate proteins. Subsequently, various treatments will be employed to selectively degrade immunoreactive epitope(s), including dissociation with ionic detergent, disulfide bond reduction using 2-mercaptoethanol, V-8 protease digestion and deglycosylation (Table 5, Steps 5–7). The loss of immunoreactivity will be measured in parallel with native envelope protein ("target" antigen) as described above.

Where glycosylation appears to play a role in the "early" HIV immune response based on antibody isotyping and endoglycosidase treatment experiments, specific glycopeptide subunits can be isolated by lectin affinity chromatography based on the carbohydrate profile of HIV (Table 5, Step 8). The carbohydrate profile of HIV is described by Geyer et al., which reference is specifically incorporated herein by reference (Geyer et al., (1988) *J. Biol. Chem.*, 262: 11760–11767). Even mild treatments are suspected to destroy the antigenic epitopes recognized by "early" HIV immune sera, especially if conformational patterns involving non-contiguous sequencs within the protein are important to antibody reactivity. Based on the observation that regions of antibody binding to proteins are resistant to proteolysis, epitopes will be mapped on HIV envelope proteins by proteolysis of antigen-antibody complexes, comparing the relative rates of release of peptides from complexed protein to that of unbound antigen using reverse-phase high-performance liquid chromatography (43) (Jemmerson et al., (1986) *Science*, 232: 1001–1004).

TABLE 5

Proposed Scheme of Characterization of HIV Envelope Epitopes
Reactive with Patients' Antibodies (1) HIV-INFECTED CELLS
→ Secreted gp120, Cytosol, Cell Membrane, Whole Cells (2) EXTRACTION OF NATIVE PROTEINS USING LOW LEVELS OF NONIONIC DETERGENT (3) Test for reactivity to patients' antibodies via immune precipitation or Western blot using non-denaturing gels or via immuno-affinity chromatography using patients' antibodies (will also use to purify proteins)

(4) EPITOPE MAPPING USING ANTIBODY BINDING (5) PROTEIN DENATURATION USING IONIC DETERGENTS (SDS) AND/OR REDUCING AGENTS (BME)

(6) PROTEOLYTIC DIGESTION USING *S. AUREUS* PROTEASE (7) DEGYLCOSYLATION USING ENDOGLYCOSIDASES, ENDO H AND PNG-ASE F (8) ISOLATION OF SPECIFIC GLYCOSYLATED PEPTIDES BY LECTIN CHROMATOGRAPHY

EXAMPLE 6

Proposed Preparation of Avirulent HIV Antigen

The present experiment describes the hypothesized molecular propagation of avirulent HIV antigen which reacts immunologically to the presence of early anti-HIV antibody in a patient sample. Absorption analysis and electrophoresis data obtained regarding the shared antigenic epitopes among HIV strains proposed to be demonstrated in Example 5 are to be used in elucidating the particular amino acid sequence of the collective "conserved" epitopes.

HIV sequence differences appear to concentrate in the env gene, which encodes the virion envelope proteins. Applicants in this study seek to determine which regions of the envelope proteins encoded by the env gene might be conserved or "shared" among a representative number of HIV isolates.

Applicants propose the production of peptide sequences to form an avirulent HIV-antigenic determinant using recombinant DNA expression vectors. These peptide sequences will function as avirulent immunoreactive epitopes as a reagent to be used in an anti-HIV antibody detection assay. The expression of these particular peptide sequences will be accomplished using recombinant DNA technology. For example, plasmid vectors containing these identified DNA segments will be used to transform a host genome to achieve gene expression and production of an avirulent HIV target antigen. Particular HIV peptide sequences will then be subcloned.

In prokaryotic cells, vectors such as pOB3, 4 and 5 containing ATG codons followed by polylinkers allowing protein expression from three potential reading frames will be used. Alternatively, the eukaryotic Baculovirus expression system will be employed using plasmids such as pVL1392, pVL1393, or pVL941 using standard methods well known to those of skill in the art of molecular genetics and as reviewed by Summers et al., (1987), *A Manual of Methods for Baculovirus Vectors and Insect Cell Culture Procedure.*, Texas A&M Press). The Summers et al. reference is hereby specifically incorporated by reference into the present specification (42). The referenced plasmids are maintained and are available from Applicants' laboratory at the University of Texas at Galveston Department of Microbiology.

EXAMPLE 7

Anti-Envelope Antibodies to Autologous HIV-1 Isolates Among HIV-p24 Seronegative Individuals This experiment was designed to determine whether the presence of anti-HIV antibodies could be detected in patient samples testing seronegative for antibodies directed against denatured HIV antigens p17, p19, p24, p27, p38, gp41, and p55 by Western Immunoblot (WB) analysis. These particular patient sera also tested negative for the presence of p24 denatured HIV antigen by antigen-capture ELISA methods currently practiced in the art.

This prospective study was performed on a group of asymptomatic HIV (+) subjects. HIV-1 was isolated from four (4) HIV EIA(−) control subjects from this group by the method outlined in Example I, supra. Each of the four subjects gave a history of sexual exposure to HIV(+) patients, while one of the four had shared needles with an HIV(+) patient. These patients are described as at "high risk" for HIV infection by virtue of the referenced activities.

Following detection of HIV-1 in the culture of lymphocytes from these patients, autologous sera samples stored from each of these patients tested negative both for HIV p24 antigen (antigen-capture ELISA), and for antibodies directed against HIV denatured antigens p17, p19, p24, p27, p38, gp41, p55 by Western Immunoblotting. These four HIV-1 isolates were adopted to continuous cell lines in culture, and the corresponding sera tested for the presence of anti-envelope (env) antibody to autologous HIV-1 by live-cell immunofluorescence on an Epics flow cytometer. The live-cell immunofluorescence assay employed is detailed at Example 4, supra.

Each of the four subjects demonstrated reactivity to autologous HIV-1, indicating the presence of autologous anti-HIV antibodies. None of the four subjects demonstrated any symptoms or signs of acute HIV infection.

These results indicate that high-risk individuals may be infected with HIV-1 and remain asymptomatic and seronegative for anti-p24, but be seropositive for env antigens. These data also suggest that antibodies directed against HIV-1 env may be important in detecting early infections with HIV, and that non-denaturing methods of preparing HIV antigen are also important.

EXAMPLE 8

Comparative Study of HIV Exposure Detection by Live HIV Virus Isolation Versus Anti-HIV Antibody The present experiment was conducted to determine the level of accuracy for detecting HIV-infection employing two particular detection methods. Samples were taken from 147 high-risk patients and tested for the presence of HIV virus itself. This method used for virus isolation is outlined by Gallo et al. (5). Of the 147 cultures, 92 were diagnosed as infected with HIV virus using the live virus detection method.

In contrast, all 147 samples when tested by the anti-HIV detection method of the present invention were determined to be seropositive (i.e., detectable anti-HIV antibody). The live-cell assay used was the fluorescence assay outlined in Example 2, supra. This data indicates detection of anti-HIV antibody by the immunofluorescence method proposed by Applicants yields more reliable HIV test results than the alternative live-virus isolation method alone.

EXAMPLE 9

Proposed Early Anti-HIV Antibody Detection Kit

The present example sets forth the proposed HIV early detection ELISA assay kit employing the proposed avirulent HIV non-denatured target antigen. The kit will comprise an autoclavable container with fittings for a Falcon 96 well microtiter plate and five vials suitable for the containment of biological assay reagents. To the bottom of each well will be absorbed a one microgram quantity (or less as advised) of non-denatured HIV antigen.

The kit will further comprise a series of five vials. A first vial is to contain a volume of PBS-tween 20 buffer. This buffer is preferably used to dilute the various reagents. A second vial is to contain a quantity of anti-immunoglobulin to anti-HIV antibody. By way of example, where mouse or rat antibodies are being detected, rabbit antiserum will be used at a dilution of about 1:100 to about 1:500. A third vial is to contain an anti-immunoglobulin, such as goat anti-rabbit IgG. This reagent is preferably used between about a 1:500 or about 1:100 dilution. The fourth vial is to contain a volume of enzyme reagent. For example, such a reagent may comprise rabbit anti-alkaline phosphatase-alkaline phosphatase soluble complexes. This particular enzyme reagent is preferably used at a dilution of between about 1:1000 to about 1:2000. The fifth vial is to include a volume of an enzymatic substrate. For example, this substrate may comprise p-nitrophenyl phosphate in 0.05M carbonate buffer, adjusted to a pH of about 9.6 (1 mg./ml. solution) with 2 mM $MgCl_2$.

EXAMPLE 10

Proposed Enzyme-Linked Immunoadsorbent Assay (ELISA) for Early HIV Exposure Detection The following example sets forth a method of detecting HIV exposure using the detection kit described in Example 9, supra.

The ELISA method of antibody detection may be performed using a solid phase or unbound to a solid support.

The sensitivity of most ELISA's like RIAs, is in the nanogram to picogram level, depending on the quality of the reagents used. Incubations longer than 1 hour and temperatures greater than 20°–25° C. have not increased the sensitivity of the assays performed in Applicants' laboratory.

The following protocol sets forth one preferred embodiment of the method to be used in detecting the presence of anti-HIV antibody in a biological sample.

Procedure

Preferably, Falcon 96 well microtiter plates are used. However, other multiple well assay plates may be used with equal effectiveness. Plates are washed with distilled $H_2O$ before use. All wells are washed with saline-tween 20 buffer between each step. 150 microliters of the appropriate reagent are to be added to each well.

Step 1. Adsorption of antigen to solid support: Adsorb one microgram of HIV non-denatured envelope antigen (or less as advised) to each well of 96 well microtiter plate. HIV-antigen is diluted in a 0.1M carbonate buffer pH 9.6 and incubated for 3 hrs. at 37° C. PBS may be substituted for adsorption.

Step 2. Addition of test sera. Dilution (1:50 to 1:10$^6$, depending on the titer) in PBS-tween 20 buffer are allowed to incubate with the immunosorbent for 1 hr. at room temperature (overnight at 4° C. for low affinity antibodies).

*Step 3. Addition of developing reagents. Each step is for 1 hr. at room temperature. Dilutions are in PBS-tween 20 buffer.

*For a direct ELISA substitute alkaline phosphatase conjugated anti-immunoglobulin into Step 3; then proceed to Step 4.

a. Anti-immunoglobulin to antibody to be measured. Usually rabbit antisera when detecting rat or mouse antibodies. Used at 1:100 to 1:500.

b. Anti-immunoglobulin bridge. Goat anti-rabbit IgG. Used at 1:500 to 1:1000.

c. Enzyme reagent. Rabbit anti-alkaline phosphatase-alkaline phosphatase soluble complexes. Used at 1:1000 or 1:2000. By way of example, such an enzyme comprises peroxidase.

Step 4. Addition of substrate. p-nitrophenyl phosphate when using alkaline phosphatase conjugates in 0.05M carbonate buffer pH 9.6 (one mg/ml solution) with 2 mM MgCl$_2$ is added and allowed to incubate at room temperature until O.D. at 400 nm is approximately 1.0 for the fastest turning well (i.e. the well which reacts first). At this time the reaction is stopped by the addition of 10 microliters of 1M NaOH. By way of example, such a substrate is diamino benzadine for peroxidase conjugates.

Step 5. Read optical density at 400 nm in plate reader or spectrophotometer.

| ELISA reaction buffer | ELISA coupling buffer |
| --- | --- |
| –8.76 gm NaCl | –3.39 gm. sodium carbonate |
| –.5 ml tween 20 | –5.70 gm sodium bicarbonate |
| –.46 gm NaH$_2$PO$_4$ | pH 9.8 |
| –1.80 gm Na$_2$PO$_4$ | H$_2$ up to one liter |
| –pH 7 | |
| H$_2$O up to one liter | |

| ELISA substrate buffer | ELISA wash for 3.5 l |
| --- | --- |
| –2.33 gm sodium carbonate | –31.5 gm NaCl |
| –2.35 gm sodium bicarbonate | –1.75 ml TWEEN 20 |
| –.20 gm MgCl$_2$ | H$_2$O up to 3.5 liters |
| H$_2$O up to one liter | |

EXAMPLE 11

Infection of Cells with HIV

The viruses set forth in the application may be used in the preparation of an HIV-infected cell culture. By way of example but not limited thereto, the types of cells which are infected with HIV include H$_9$, CEM or Jurket cells. Analogous cell types may be similarly so infected with the described viruses. The HIV-infected cell culture comprise the "target" antigen of the subject anti-HIV antibody detection system.

Cells are infected with an HIV virus selected from the following group of viruses:

| HIV$_{PM16}$; | HIV$_{MCK}$; | HIV III |
| --- | --- | --- |
| HIV$_{PM205}$; | HIV$_{AK-1}$; | |
| HIV$_{213}$; | HIV$_{SK-1}$; | |
| HIV$_{ED-1}$; | HIV$_{AC-1}$; | |
| HIV$_{TP-1}$; | HIV$_{214}$; | |
| HIV$_{CP-1}$; | HIV$_O$; | |
| | HIV$_{G1}$; | and |

Specifically, approximately 12 million cells are first obtained in culture. To these cells is added about 15 mls. of HIV-virus stock. The HIV-virus stock constitutes about 10$^5$ to 10$^6$ infectious units/ml. The cells and virus are incubated from 10–14 hours (overnight). The culture of cells and virus is then pelleted and the supernatant discarded. The pellet of cells and virus is then resuspended in fresh culture media. The culture is then monitored at least once a week for the presence of HIV-antigen. The presence of HIV-antigen can be detected by a number of methods, including live-cell immunofluorescence, using serum samples containing anti-HIV antibodies.

Changes may be made in the construction, operation and arrangement of the various parts, elements, steps and procedures described herein without departing from the scope of the invention as defined in the following claims.

The following references are cited at various points throughout the specification and are specifically incorporated by reference in pertinent part into the present specification.

BIBLIOGRAPHY

1. Barre-Sinoussi et al., (1983), *Science,* 220:868–871.
2. Popovic et al., (1984), *Science,* 224:497–500.
3. Coffin et al., (1986), *Nature,* 321:10.
4. Centers for Disease Control, (1982), *New Engl. J. Med.,* 306:248–252, Task Force on Kaposi Sarcoma and Opportunistic Infections.
5. Gallo et al., (1984), *Science,* 224:500–503.
6. Saag et al., (1986), *N. Engl. J. Med.,* 314:1118.
7. Burke et al., (1986), *JAMA,* 256:347.
8. Chou et al., (1988), *J. Infect. Disease,* 157(4):805–811.
9. Barin et al., (1985), *Science,* 228:1094–1096.
10. Kitchen et al., (1986), *J. Infect. Dis.,* 153:788–790.
11. Salahuddin et al., (1984), *Lancet,* 2:1418–1420.
12. Mayer et al., (1986), *Ann. Intern. Med.,* 104:194–196.
13. Groupman et al., (1985), *Blood,* 66:742–744.
14. Ranki et al., (1987), *Lancet,* 2:589–593.
15. Wolinsky et al., (1988), Fourth International Conference on AIDS, Stockholm, Abstract No. 1099, pg. 137.
16. Loche, et al., (1988), *Lancet,* 2:418–421.
17. Imagawa, et al., (1989), *New J. Med.,* 320(22):1458–1489.
18. Monastersky (Jun. 3, 1989), *Science News,* 135:340.
19. *Dupont Bioteck Update,* (May 1989), "Improved HIV p24 Core Profile ELISA"; NEK-060, NEK-060A.
20. Allain et al. (1986), *Lancet,* Nov. 29, 1986:1233–1235
21. Goudsmit et al. (1987) *J. Inf. Disease,* 155(3):558–560
22. Franchini et al. (1987), *Blood,* 69(2):437–441.
23. Sarngadharan et al. (1984), *Science,* 224:506–508.
24. Hofbauer et al. (Jan. 1988), *J. Clin. Micro.,* 26(1):116–120.
25. Ujehlyi et al. (1987), *AIDS,* 1:161–165.
26. Shepp et al. (1987), *AIDS,* 2:113–117.
27. Lange et al. (1987), *AIDS* 1:15–20.
28. Ferroni et al. (1988), *Vox Sang,* 55:143–147.
29. Harada et al. (1987), *Virology,* 158:447–451.
30. Weiss, R. (1989), *Science News,* 135:340.
31. U.S. Pat. No. 4,725,669—Essex
32. Huisman et al. (1987), *Vox Sang,* 53:31–36.
33. DiMarzo et al. (1985), *Proc. Natl. Acad. Sci.,* 82:5199–5202.
34. Lasky et al. (1986), *Science,* 233:209–233.
35. Cloyd et al. (1977), *J. Clin. Microb.,* 5(1):86–90.
36. Cloyd et al. (1987), *Virology,* 161:286–292.
37. U.S. Pat. No. 4,722,888—Broder (Feb. 2, 1988).

38. Miles et al. (1968), *Nature,* 219:186.
39. Butler et al. (1978), *Immunochemistry,* 15:131–136.
40. Haseltine, W. W. (1989), *New Eng. J. Med.,* 320:1487–1489.
41. Popovich et al. (1984), *Science,* 224:497.
42. Summers et al. (1987), *A Manual of Methods for Baculovirus Vectors and Insect Cell Culture Procedure,* Texas A&M Press.
43. Jemmerson et al. (1986), *Science,* 232:1001–1004.
44. Poiesz et al. (1980), *Proc. Natl. Acad. Sci., U.S.A.,* 77:7415.
45. Berson & Yalow.
46. Robert-Guroff, et al. (1985), *Nature,* 316:72–74.
47. Cloyd et al. (1979), *J. Exp. Med.,* 149:702–712.
48. Laemmli (1970), *Nature,* 227:680–685.
49. Robey et al., (186), *Proc. Natl. Acad. Sci. USA,* 84:7023–7027.

What is claimed is:

1. An immunological method for detecting early human anti-HIV antibodies in a biological sample comprising the steps of:
   preparing a target antigen with preserved configurational integrity of HIV envelope antigen that binds early anti-HIV antibody;
   contacting a quantity of the target antigen with a biological sample to form a mixture;
   incubating the mixture to facilitate binding between the target antigen and any early anti-HIV antibodies present in said biological sample specific for the target antigen to form a reaction mixture; and
   adding a labeled anti-HIV secondary antibody to label early antibody bound to the target antigen in the reaction mixture to produce labeled antibody target antigen complexes;
wherein the presence of labeled antibody-target antigen complexes provide an early indication of HIV exposure, and which biological sample is negative for early anti-HIV antibody to denatured HIV antigen by Western Blot or ELISA.

2. A method for detecting early human anti-HIV antibody in serum sample comprising a live-cell immunofluorescence assay including the steps of:
   preparing a target antigen of HIV-infected cells;
   pelleting the HIV-infected cells to form a first cell pellet;
   resuspending the first pellet with a volume of a serum sample from a patient to form a mixture;
   incubating the mixture to form a first incubate;
   pelleting the first incubate to form a second pellet;
   resuspending the second pellet in a non-denaturing buffer to form a mixture;
   incubating the mixture;
   pelleting the mixture and non-denaturing buffer to form a third pellet;
   resuspending the third pellet with a volume of labeled anti-HIV secondary antibody to form a mixture;
   incubating the resuspended mixture to form a second incubate;
   pelleting the second incubate to form a fourth pellet;
   resuspending the fourth pellet in a volume of non-denaturing buffer to form a mixture;
   incubating the mixture;
   pelleting the mixture to form a fifth pellet; and
   fixing the fifth pellet with a formalin solution
wherein the presence of labeled cells indicates the presence of early anti-HIV antibodies in the biological sample and an early indicating of HIV exposure, and which biological sample is negative for anti-HIV antibody to denatured HIV antigen by Western Blot or ELISA.

3. The method of claim 2 wherein the formalin solution is further defined as a 2% formalin solution.

4. The method of claim 2 wherein the labeled anti-HIV secondary antibody is FITC-conjugated anti-human polyvalent IgG.

5. The method of claim 2 wherein the non-denaturing buffer comprises a phosphate buffer.

6. The method of claim 1 wherein the biological sample is a blood sample.

7. The method of claim 1 wherein the biological sample is blood serum.

8. The method of claim 6 wherein the biological sample is human blood serum.

9. The method of claim 2, wherein the target antigen comprises cells infected with a human immunodeficiency virus selected from the group consisting of: $HIV_{213}$; $HIV_{TP-1}$; and $HIV_{AC-1}$.

10. The method of claim 2 where the target antigen comprises cells infected with $HIV_{AC-1}$ or $HIV_{TP-1}$ human immunodeficiency virus.

11. The method claim 10 where the $HIV_{AC-1}$ is ATCC #VR2246 and the $HIV_{TP-1}$ is ATCC #VR2245.

12. The method of claim 2 wherein the resuspended mixture of the first pellet is incubated for at least about 45 minutes.

13. The method of claim 2 where the target antigen comprises H9 cells infected with the human immunodeficiency virus.

* * * * *

UNITED STATES PATENT AND TRADEMARK OFFICE
CERTIFICATE OF CORRECTION

PATENT NO. : 5,587,285
DATED : December 24, 1997
INVENTOR(S) : Miles W. Cloyd, et al.

It is certified that error appears in the above-indentified patent and that said Letters Patent is hereby corrected as shown below:

In claim 9, column 26, line 38-39, delete "$HIV_{TP-1}$".

Signed and Sealed this

Twentieth Day of May, 1997

*Attest:*

BRUCE LEHMAN

*Attesting Officer*      *Commissioner of Patents and Trademarks*